United States Patent [19]

Güngör et al.

[11] Patent Number: 5,723,485
[45] Date of Patent: Mar. 3, 1998

[54] 1,2-DIARYLINDOLE DERIVATIVES, PROCESSES FOR THEIR PREPARATION AND THEIR USES IN THERAPEUTICS

[75] Inventors: Timur Güngör, Rueil Malmaison; Jean-Marie Teulon, La Celle Saint Cloud, both of France

[73] Assignee: Laboratories UPSA, Agen, France

[21] Appl. No.: 723,450

[22] Filed: Oct. 7, 1996

[30] Foreign Application Priority Data

Aug. 1, 1996 [FR] France .................... 96 09741

[51] Int. Cl.⁶ .................... A61K 31/40; C07D 209/08
[52] U.S. Cl. .................... 514/415; 514/414; 514/339; 546/277.4; 548/465; 548/503; 548/511
[58] Field of Search .................... 548/465, 503, 548/511; 514/415, 414, 339; 546/277.4; 424/456, 464

[56] References Cited

U.S. PATENT DOCUMENTS 5,496,844  3/1996  Inai et al. .................... 514/415

*Primary Examiner*—Joseph McKane
*Attorney, Agent, or Firm*—Aldo A. Algieri

[57] ABSTRACT

The present invention relates to the derivatives of the formula

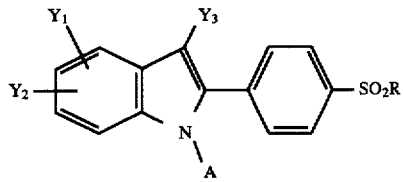

and to their use in therapeutics, especially as drugs with anti-inflammatory and analgesic properties.

12 Claims, No Drawings

1,2-DIARYLINDOLE DERIVATIVES, PROCESSES FOR THEIR PREPARATION AND THEIR USES IN THERAPEUTICS

The present invention relates to the 1,2-diarylindole derivatives of general formula (I) as novel products.

One of the arachidonic acid biotransformation pathways is the cyclooxygenase pathway, which makes it possible to transform arachidonic acid to PGG2 and then PGH2. Recent work on the cloning and sequencing of cyclooxygenase has revealed the presence of two isoenzymes, namely cyclooxygenase-1 (COX-1) and cyclooxygenase-2 (COX-2), in several species and particularly in man. The first is a constitutive enzyme which is expressed in the majority of tissues, while the second, which is expressed in a few tissues such as the brain, is inducible in the majority of tissues by numerous products, in particular by the cytokines and the mediators produced during the inflammatory reaction. Each enzyme has a different role and the inhibition of COX-1 or COX-2 will not have identical consequences. The inhibition of COX-1 will cause a decrease in the prostaglandins participating in homeostasis, which can give rise to side effects. The inhibition of COX-2 will cause a decrease in the prostaglandins produced in an inflammatory situation. Thus the selective inhibition of COX-2 makes it possible to obtain a well-tolerated anti-inflammatory.

The compounds of the invention make it possible to achieve this selective inhibition. The compounds in question consequently have a very valuable pharmacological profile insofar as they possess anti-inflammatory and analgesic properties while being remarkably well tolerated, especially in gastric terms. They will be particularly indicated in the treatment of inflammatory phenomena and in the treatment of pain.

An example of their use which may be mentioned is the treatment of arthritis, especially rheumatoid arthritis, spondylitis, gouty arthritis, osteoarthritis, juvenile arthritis, autoimmune diseases and lupus erythematosus. They will also be indicated in the treatment of bronchial asthma, dysmenorrhea, tendinitis, bursitis and dermatological inflammations such as psoriasis, eczema, burns and dermatitis. They can also be used for the treatment of gastrointestinal inflammations, Crohn's disease, gastritis and ulcerative colitis.

Their analgesic properties also enable them to be used for any pain symptoms, especially in the treatment of myalgia, articular pain or neuralgia, dental pain, herpes zoster and migraine, in the treatment of rheumatic complaints and pain of cancerous origin, and also as complementary treatments for infectious and febrile states.

The present invention further relates to the process for the preparation of said products and to their applications in therapeutics.

These 1,2-diarylindole derivatives have general formula (I):

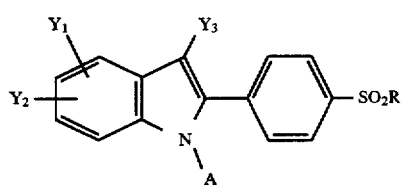

Formula (I)

in which:
R is:
  a lower alkyl radical having 1 to 6 carbon atoms,
  a lower halogenoalkyl radical having 1 to 6 carbon atoms, or
  a group —$NH_2$;
A is:
  an aromatic ring:

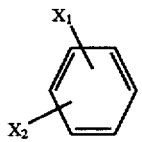

in which $X_1$ and $X_2$ independently are:
  the hydrogen atom,
  a halogen atom,
  a lower alkyl radical having 1 to 6 carbon atoms,
  a trifluoromethyl radical,
  a radical $(CH_2)_n NR_1 R_2$, in which:
    n is an integer from 0 to 2, and
    $R_1$ and $R_2$ independently are the hydrogen atom or a lower alkyl radical having 1 to 6 carbon atoms,
  a lower O-alkyl radical having 1 to 6 carbon atoms, or
  a group $SO_2R$, R being as defined above,
  or else $X_1$ and $X_2$ together form a methylenedioxy group;
A can also be a thiophene or pyridine heterocycle;
$Y_1$ and $Y_2$ independently are:
  the hydrogen atom,
  a halogen atom,
  a lower alkyl radical having 1 to 6 carbon atoms, or
  a group $SO_2R$, R being as defined above; and
$Y_3$ is:
  the hydrogen atom or
  a lower alkyl, radical having 1 to 6 carbon atoms.

In the description and the claims, lower alkyl is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

Lower haloalkyl radical is understood as meaning an alkyl radical having 1 to 6 carbon atoms in which 1 to 7 hydrogen atoms have been substituted by 1 to 7 halogen atoms. A lower haloalkyl radical is for example a trifluoromethyl radical, a 2,2,2-trifluoroethyl radical, a pentafluoroethyl radical, a 2,2-difluoro-3,3,3-trifluoropropyl radical, a heptafluoropropyl radical or a chloromethyl or bromomethyl radical.

Halogen is understood as meaning a chlorine, bromine, iodine or fluorine atom.

The derivatives according to the invention are advantageously the derivatives of formula (I) above in which:
R is a lower alkyl radical having 1 to 6 carbon atoms;
A is an aromatic ring:

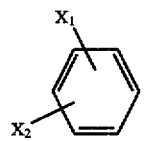

in which $X_1$ and $X_2$ independently are:
  the hydrogen atom,
  a halogen atom,
  a lower alkyl radical having 1 to 6 carbon atoms, or
  a radical $(CH_2)_n NR_1 R_2$ in which:
    n is equal to 1 and $R_1$ and $R_2$ are a lower alkyl radical having 1 to 6 carbon atoms;

A can also be a thiophene heterocycle;

$Y_1$ and $Y_2$ independently are:

the hydrogen atom,
a halogen atom,
a lower alkyl radical having 1 to 6 carbon atoms, or
a group $SO_2R$, R being as defined above; and $Y_3$ is:

the hydrogen atom or
a lower alkyl radical having 1 to 6 carbon atoms.

Within the framework of the present invention, it will be advantageous to use a compound of formula (I) in which at least one of the following conditions is satisfied:

R is a methyl radical;

A is an aromatic ring:

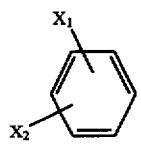

in which:

$X_1$ is the hydrogen atom, the fluorine atom, the chlorine atom or a methyl radical and $X_2$ is the hydrogen atom;

$Y_1$ is the hydrogen atom;

$Y_2$ is the hydrogen atom; and $Y_3$ is the hydrogen atom.

The particularly preferred compounds of the invention are as follows:

1-(4-fluorophenyl)-2-[4-(methylsulfonyl)phenyl]indole

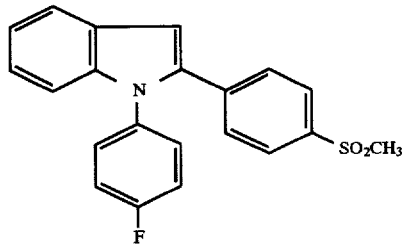

1-(4-chlorophenyl)-2-[4-(methylsulfonyl)phenyl]indole

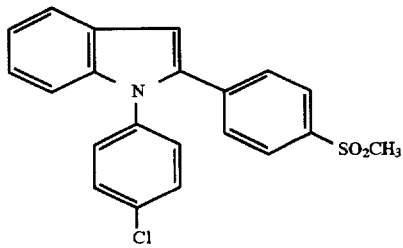

1-(4-methylphenyl)-2-[4-(methylsulfonyl)phenyl]indole

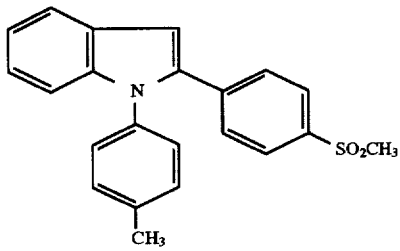

1-phenyl-2-[4-(methylsulfonyl)phenyl]indole

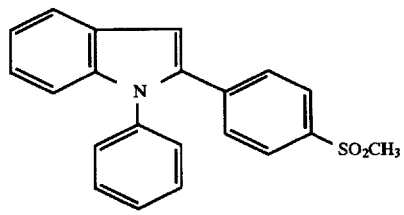

The compounds of formula (I) of the invention can be obtained from derivatives of formula (II):

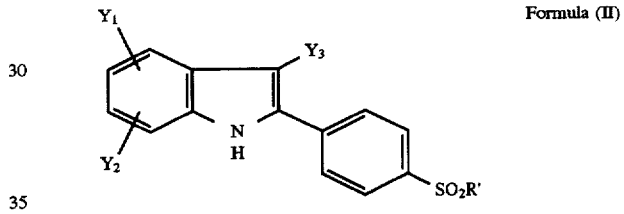

Formula (II)

in which:

$Y_1$, $Y_2$ and $Y_3$ are as defined above and R' is a lower alkyl radical having 1 to 6 carbon atoms or a lower haloalkyl radical having 1 to 6 carbon atoms, by reaction with the compounds of formula (III):

A-X  Formula (III)

where A is an aromatic ring:

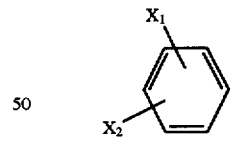

in which $X_1$ and $X_2$ are as defined above, or a thiophene or pyridine heterocycle, and where X is a halogen atom, under the conditions described in the literature and illustrated for example by the following references:

Khan, M. A. and Rocha, E. K., Chem. Pharm. Bull. 1977, 3110.

Unangst, P. C., Connor, D. T., Stabler, S. R. and Weikert, R. J., J. Het. Chem. 87, 814.

Unangst, P. C., Connor, D. T. and Stabler, S. R., J. Het. Chem. 1987, 818.

Saleha, S., Siddiqui, A. A. and Khan, N. H., Ind. J. Chem. 1980, vol. 19B, 198, p. 81.

The compounds of formula (I) of the invention in which R is a group $NH_2$ can be obtained from derivatives of formula (I) in which $Y_1$, $Y_2$, $Y_3$ and A are as defined above and R is the methyl group:

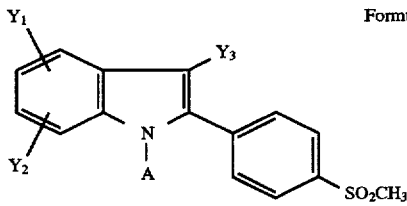

Formula (I, R = CH₃)

by any one of the methods known in the literature for converting methyl sulfones to sulfonamides, for example the method described in Tetrahedron Letters, 1994, vol. 39, no. 35, 7201, which consists in reacting the methyl sulfones with a base and a trialkylborane in an organic solvent, such as tetrahydrofuran, under reflux, and then reacting the product with hydroxylamine-O-sulfonic acid.

The compounds of formula (II) are obtained by the classical synthesis of indoles, as described in the following literature references:

- E. Fischer, F. Jourdan, Ber. 1883, 16, 2241
- E. Fischer, O. Hess, Ber. 1884, 17, 559
- B. Robinson, Chem. Rev. 1963, 63, 372
- B. Robinson, Chem. Rev. 1969, 69, 227
- B. Robinson, The Fischer Indole Synthesis (Wiley, New York, 1982) from hydrazone derivatives of formula (IV):

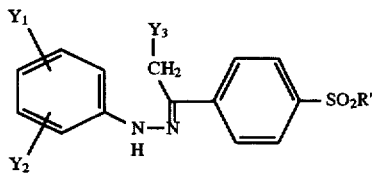

Formula (IV)

in which $Y_1$, $Y_2$, $Y_3$ and R' are as defined above, by heating in the presence of a catalyst such as zinc chloride or another Lewis acid, or else in the presence of a protonic acid such as sulfuric acid or polyphosphoric acid (PPA).

The compounds of formula (IV) are obtained in conventional manner by condensing a hydrazine of formula (V):

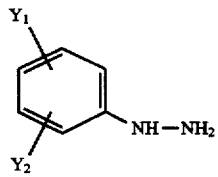

Formula (V)

in which $Y_1$ and $Y_2$ are as defined above, with ketones of formula (VI):

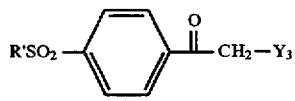

Formula (VI)

in which $Y_3$ and R' are as defined above.

The derivatives of formula (VI) are prepared from compounds of formula (VII):

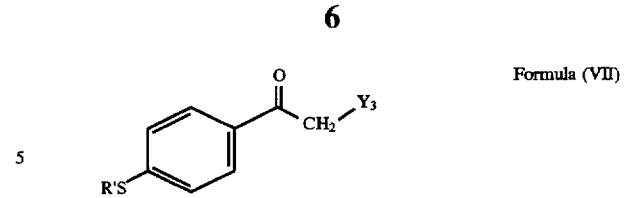

Formula (VII)

in which $Y_3$ and R' are as defined above, by means of an oxidation reaction with a peracid such as m-chloroperbenzoic acid, in an organic solvent such as dichloromethane, or with an inorganic oxidizing agent such as potassium permanganate or sodium perborate, in a solvent such as acetic acid.

The compounds of formula (VII), in which R' and $Y_3$ are as defined above, are prepared from derivatives of formula (VIII):

Formula (VIII)

in which R' is as defined above, by means of a Friedel-Crafts reaction in the presence of $AlCl_3$ or another Lewis acid with the acid chloride of formula (IX):

Formula (IX)

in which $Y_3$ is as defined above.

In the case where $Y_3$ is the hydrogen atom, the acetophenone compounds of formula (VII) may also be obtained by the method described in Organic Synthesis Coll. vol. 4, 1963, p. 708, from acids of formula (X):

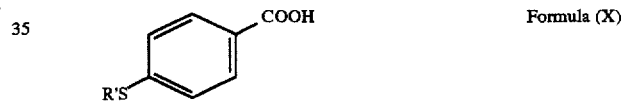

Formula (X)

in which R' is as defined above, said acids being known in the literature.

This method consists in reacting the chloride of the acids of formula (X) with ethoxymagnesium diethylmalonate.

The compounds of formula (I) as defined above are cyclooxygenase-2 inhibitors and possess a very good anti-inflammatory and analgesic activity coupled with an excellent tolerance, particularly gastric tolerance.

These properties justify their application in therapeutics and the invention further relates, by way of drugs, to the products as defined by formula (I) above.

Thus the invention also covers a pharmaceutical composition characterised in that it comprises a pharmaceutically effective amount of at least one compound of formula (I) as defined above, optionally incorporated in a pharmaceutically acceptable excipient, vehicle or carrier.

These compositions can be administered by the buccal, rectal, parenteral, transdermal, ocular, nasal or auricular route.

These compositions can be solid or liquid and can be presented in the pharmaceutical forms commonly used in human medicine, for example simple or coated tablets, gelatin capsules, granules, suppositories, injectable preparations, transdermal systems, eye drops, aerosols and sprays, and ear drops. They are prepared by the customary methods. The active principle, which consists of a pharmaceutically effective amount of at least one compound of formula (I) as defined above, can be incorporated therein together with excipients normally employed in pharmaceutical compositions, such as talc, gum arabic, lactose, starch, magnesium stearate, polyvidone, cellulose derivatives, cocoa butter, semisynthetic glycerides, aqueous or non-aqueous vehicles, fats of animal or vegetable origin, glycols, various wetting agents, dispersants or emulsifiers, silicone gels, certain polymers or copolymers, preservatives, flavorings and colors.

The invention also covers a pharmaceutical composition with anti-inflammatory and analgesic activity which can be used especially as a favorable treatment for inflammatory phenomena and pain, said composition comprising a pharmaceutically effective amount of at least one compound of formula (I) above, optionally incorporated in a pharmaceutically acceptable excipient, vehicle or carrier.

In one embodiment, a pharmaceutical composition with anti-inflammatory and analgesic activity is prepared which can be used especially as a favorable treatment for various inflammations and pain.

In one variant, a composition is formulated as gelatin capsules or tablets containing a dose of 1 mg to 1000 mg, or as injectable preparations containing a dose of 0.1 mg to 500 mg. It is also possible to use compositions formulated as suppositories, ointments, creams, gels, aerosol preparations, transdermal preparations or plasters.

The invention also covers a method of therapeutic treatment for mammals, wherein a therapeutically effective amount of at least one compound of formula (I) as defined above is administered to said mammal. In one variant of this method of treatment, the compound of formula (I), either by itself or in association with a pharmaceutically acceptable excipient, is formulated as gelatin capsules or tablets containing a dose of 1 mg to 1000 mg for oral administration, as injectable preparations containing a dose of 0.1 mg to 500 mg or as suppositories, ointments, creams, gels or aerosol preparations.

This method affords especially a favorable treatment for inflammatory phenomena and pain.

In human and animal therapeutics, the compounds of formula (I) can be administered, by themselves or in association with a physiologically acceptable excipient, in any form, in particular orally in the form of gelatin capsules or tablets, or parenterally in the form of injectable solutions. It is possible to envisage other forms of administration such as suppositories, ointments, creams, gels or aerosol preparations.

As will be clearly apparent from the pharmacological experiments given at the end of the description, the compounds according to the invention can be administered in human therapeutics, in the above-mentioned indications, orally in the form of tablets or gelatin capsules containing a dose of 1 mg to 1000 mg, or parenterally in the form of injectable preparations containing a dose of 0.1 mg to 500 mg, in one or more daily dosage units, for an adult with an average weight of 60 to 70 kg.

In animal therapeutics, the daily dose which can be used is between 0.1 mg and 100 mg per kg.

Further characteristics and advantages of the invention will be understood more clearly from the following Examples, which in no way imply a limitation but are given by way of illustration.

EXAMPLE 1

4-(Methylsulfonyl)fluorobenzene

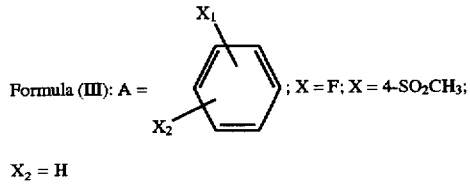

Formula (III): A = ; X = F; X = 4-SO$_2$CH$_3$;

X$_2$ = H 50 g (0.44 mol) of methanesulfonyl chloride are introduced dropwise into a mixture of 150 ml of fluorobenzene and 58.3 g (0.4 mol) of AlCl$_3$. After 7 h under reflux, the reaction medium is poured into a mixture of water and ice. It is extracted with dichloromethane. The combined organic phases are washed with sodium bicarbonate solution, dried over MgSO$_4$ and concentrated.

The white solid obtained is purified by recrystallization from water to give 46.9 g of 4-(methylsulfonyl) fluorobenzene.

Empirical formula: C$_7$H$_7$FO$_2$S; Melting point: 73° C.

EXAMPLE 2

4-(Methylsulfonyl)acetophenone

Y$_3$=H; R'=CH$_3$  Formula (VI)

Method A

EXAMPLE 2a

Ethoxymagnesium Diethylmalonate

A mixture of 2.7 ml of ethanol and 0.3 ml of CCl$_4$ is added dropwise to 2.9 g (0.12 mol) of magnesium which has been degreased with ether. 41 ml of anhydrous ether are introduced dropwise, followed by 20 g (0.125 mol) of ethyl malonate, the solvents being kept at the reflux point without heating. When the addition has ended, the mixture is refluxed for 5 h until the magnesium has completely disappeared.

The compound is used without purification in the next step.

EXAMPLE 2b 4-(Methylsulfonyl)acetophenone

Y$_3$=H; R'=CH$_3$  Formula (VI)

22.6 g of 4-methylsulfonylbenzoyl chloride (obtained from 20 g of 4-methylsulfonylbenzoic acid refluxed for 3 h in the presence of 15 ml of SOCl$_2$, 150 ml of toluene and a few drops of pyridine, the excess toluene and SOCl$_2$ being distilled and the residue being taken up with isopropyl ether to give 22.6 g of a white solid melting at 129° C.), dissolved in 200 ml of hot benzene, are added to 28 g of ethoxymagnesium diethylmalonate obtained according to Example 2a.

The reaction mixture is heated in a water bath for 30 min. After cooling, 18 ml of concentrated H$_2$SO$_4$ diluted with 150 ml of water are introduced. The mixture is stirred for 1 h and decanted. The organic phase is washed with water until the pH becomes neutral, dried over MgSO$_4$ and concentrated. The oil obtained is taken up with a mixture of 100 ml of concentrated HCl, 100 ml of acetic acid and 50 ml of water. The resulting mixture is refluxed for 3 h, diluted with 500 ml of water and extracted with chloroform. The organic phases are combined, washed with sodium bicarbonate solution and then dried over $MgSO_4$ and concentrated.

This gives 15.1 g of 4-(methylsulfonyl)acetophenone.

Empirical formula: $C_9H_{10}O_3S$; Melting point: 127° C.

Method B

EXAMPLE 2c 4-(Methylthio)acetophenone

R'=$CH_3$; $Y_3$=H        Formula (VII)

123 g (0.92 mol) of $AlCl_3$ are added with a spatula to a mixture of 100 g (0.8 mol) of thioanisole, 750 ml of $CH_2Cl_2$ and 63 ml (0.9 mol) of acetyl chloride, cooled to 0° C. beforehand, said addition being carried out so that the temperature does not exceed 10° C. The mixture is stirred for 1 h at room temperature, heated for 1 h at 40° C. and then poured into 800 ml of an ice/water mixture. The resulting mixture is separated and extracted with $CH_2Cl_2$. The organic phases are combined, washed with water and then dried over $MgSO_4$ and concentrated to give 117.1 g of 4-(methylthio) acetophenone.

Empirical formula: $C_9H_{10}OS$; Melting point: 80° C.

EXAMPLE 2d 4-(Methylsulfonyl)acetophenone

R'=$CH_3$; $Y_3$=H Formula (VI)

A solution of 152 g (0.96 mol) of $KMnO_4$ in 3.5 l of water is introduced into a mixture of 117.1 g (0.7 mol) of 4-(methylthio)acetophenone, prepared in Example 2c, and 292 ml of acetic acid. 2.3 l of water are added and the reaction temperature is allowed to return to room temperature. Saturated sodium sulfite solution is added dropwise until the solution is decolorized. This is left to stand overnight at room temperature. The solid obtained is filtered off, washed copiously with water and recrystallized from 95% ethanol to give 91.5 g of 4-(methylsulfonyl)acetophenone.

Empirical formula: $C_9H_{10}O_3S$; Melting point: 126° C.

The compound of Example 3 was prepared by following the procedure of Examples 2c and 2d using the appropriate acid chloride.

EXAMPLE 3

1-[4-(Methylsulfonyl)phenyl]propanone

R'=$CH_3$; $Y_3$=$CH_3$        Formula (VI)

Empirical formula: $C_{10}H_{12}O_3S$; Melting point: 107° C.

EXAMPLE 4

4-(Methylsulfonyl)acetophenone Phenylhydrazone

R'=$CH_3$; $Y_1$=$Y_2$=$Y_3$=H        Formula (IV)

A mixture of 15.1 g (0.076 mol) of 4-(methylsulfonyl) acetophenone, prepared in Example 2b or 2d, 86 ml (0.088 mol) of phenylhydrazine and 80 ml of toluene is refluxed for 4 h. The water foraged during the reaction is removed by means of a Dean-Stark apparatus. This gives 20.7 g of 4-(methylsulfonyl)acetophenone phenylhydrazone.

Empirical formula: $C_{15}H_{16}N_2O_2S$; Melting point: 175° C.

The compounds of Examples 5 to 9 were prepared by following the procedure of Example 4 using the appropriate ketones and hydrazines.

EXAMPLE 5

4-(Methylsulfonyl)acetophenone 4-Chlorophenylhydrazone

R'=$CH_3$; $Y_1$=4-Cl; $Y_2$=$Y_3$=H        Formula (IV)

Empirical formula: $C_{15}H_{15}ClN_2O_2S$; Melting point: 163° C.

EXAMPLE 6

4-(Methylsulfonyl)acetophenone 4-(Methylsulfonyl)phenylhydrazone

R'=$CH_3$; $Y_1$=4-$SO_2CH_3$; $Y_2$=$Y_3$=H        Formula (IV)

Empirical formula: $C_{16}H_{18}N_2O_4S_2$; Melting point: 285° C.

EXAMPLE 7

1-[4-(Methylsulfonyl)phenyl]propanone Phenylhydrazone

R'=$CH_3$; $Y_1$=$Y_2$=H; $Y_3$=$CH_3$        Formula (IV)

Empirical formula: $C_{16}H_{18}N_2O_2S$; Melting point: 149° C.

EXAMPLE 8

4-(Methylsulfonyl)acetophenone 3,5-Dichlorophenylhydrazone

R'=$CH_3$; $Y_1$=3-Cl; $Y_2$=5-Cl; $Y_3$=H        Formula (IV)

Empirical formula: $C_{15}H_{14}Cl_2N_2O_2S$; Melting point: 218°–219° C.

EXAMPLE 9

4-(Methylsulfonyl)acetophenone 4-Methylphenylhydrazone

R'=$CH_3$; $Y_1$=4-$CH_3$; $Y_2$=$Y_3$=H        Formula (IV)

Empirical formula: $C_{16}H_{18}N_2O_2S$; Melting point: 204° C.

EXAMPLE 10

2-[4-(Methylsulfonyl)phenyl]indole

R'=$CH_3$; $Y_1$=$Y_2$=$Y_3$=H        Formula II 87.3 g (0.3 mol) of 4-(methylsulfonyl) acetophenone phenylhydrazone, prepared in Example 4, are added in portions to 613 g of polyphosphoric acid (PPA) heated to 40° C. beforehand. The temperature of this mixture is kept at 100° C. for 1 h and then at 135° C. for 10 min. 345 ml of water are added dropwise, the temperature being kept at about 80° C. The mixture is allowed to cool and neutralized with 1300 ml of 50% KOH. The precipitate is filtered off, washed with water, dried and recrystallized from methoxyethanol to give 40.8 g of 2-[4-(methylsulfonyl)phenyl] indole.

Empirical formula: $C_{15}H_{13}NO_2S$; Melting point: 250° C.

A second crop of 34.1 g can be obtained by concentration of the mother liquors.

The compounds of Examples 11 to 15 were prepared according to Example 10 using the appropriate hydrazones.

EXAMPLE 11

5-Chloro-2-[4-(methylsulfonyl)phenyl]indole

R'=$CH_3$; $Y_1$=5-Cl; $Y_2$=$Y_3$=H        Formula (II)

EXAMPLE 12

5-(Methylsulfonyl)-2-[4-(methylsulfonyl)phenyl]indole

R'=CH$_3$; Y$_1$=5-SO$_2$CH$_3$; Y$_2$=Y$_3$=H    Formula (II)

Empirical formula: C$_{16}$H$_{15}$NO$_4$S$_2$; Melting point: 325° C.

EXAMPLE 13

3-Methyl-2-[4-(methylsulfonyl)phenyl]indole

R'=CH$_3$; Y$_1$=Y$_2$=H; Y$_3$=CH$_3$    Formula (II)

Empirical formula: C$_{16}$H$_{15}$NO$_2$S; Melting point: 184° C.

EXAMPLE 14

4,6-Dichloro-2-[4-(methylsulfonyl)phenyl]indole

R'=CH$_3$; Y$_1$=4-Cl; Y$_2$=6-Cl; Y$_3$=H    Formula (II)

Empirical formula: C$_{15}$H$_{11}$Cl$_2$NO$_2$S; Melting point: 263°–264° C.

EXAMPLE 15

5-Methyl-2-[4-(methylsulfonyl)phenyl]indole

R'=CH$_3$; Y$_1$=5-CH$_3$; Y$_2$=Y$_3$=H    Formula (II)

Empirical formula: C$_{16}$H$_{15}$NO$_2$S; Melting point: 249° C.

EXAMPLE 16

1-(4-Fluorophenyl)-2-[4-(methylsulfonyl)phenyl]indole

R=CH$_3$; Y$_1$=Y$_2$=Y$_3$=H;    Formula (I)

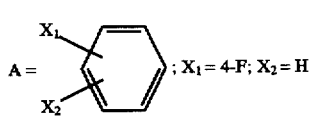

A mixture of 5 g (0.018 mol) of 2-[4-(methylsulfonyl)phenyl]indole, obtained in Example 10, 6.7 ml (0.061 mol) of 4-fluorobromobenzene, 50 ml of N-methylpyrrolidone (NMP), 2.1 g (0.02 mol) of Na$_2$CO$_3$ and 5.7 g (0.02 mol) of Cu$_2$Br$_2$ is heated at 200° C. under a nitrogen atmosphere for 7 h. The reaction is monitored by thin layer chromatography (TLC). A further 3 ml of 4-fluorobromobenzene are added and the reaction is continued for 5 h. After cooling, the reaction mixture is poured into a mixture of ml of water and to ml of ethylenediamine. Ethyl acetate is added. The mixture is filtered on Célite to remove the copper salts and the filtrate is extracted with ethyl acetate. The organic phases are combined, washed with water until the pH is neutral, and then dried over MgSO$_4$ and concentrated.

The compounds of Examples 17 to 27 were prepared by following the procedure of Example 16.

EXAMPLE 17

1-(4-Methylphenyl)-2-[4-(methylsulfonyl)phenyl]indole

R=CH$_3$; Y$_1$=Y$_2$=Y$_3$=H;    Formula (I)

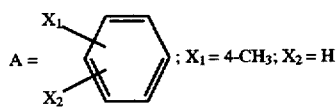

Purified by chromatography on silica gel (eluent: toluene 95%/ethyl acetate 5%).

Empirical formula: C$_{22}$H$_{19}$NO$_2$S; Melting point: 186° C.

EXAMPLE 18

1-Phenyl-2-[4-(methylsulfonyl)phenyl]indole

R=CH$_3$; Y$_1$=Y$_2$=Y$_3$=H;    Formula (I)

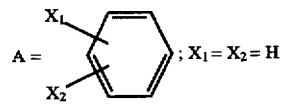

Purified by chromatography on silica gel (eluent: toluene 95%/ethyl acetate 5%).

Empirical formula: C$_{21}$H$_{17}$NO$_2$S; Melting point: 175° C.

EXAMPLE 19

1-(4-Chlorophenyl)-2-[4-(methylsulfonyl)phenyl]indole

R=CH$_3$; Y$_1$=Y$_2$=Y$_3$=H;    Formula (I)

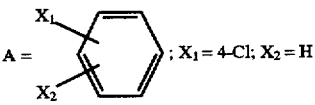

Purified by silica gel chromatography in three successive elutions (eluent: toluene 90%/ethyl acetate 10%, then toluene 95%/ethyl acetate 5% and finally chloroform 95%/isopropylamine 5%) and then recrystallized from acetonitrile.

Empirical formula: C$_{21}$H$_{16}$ClNO$_2$S; Melting point: 174° C.

EXAMPLE 20

5-(Methylsulfonyl)-2-[4-(methylsulfonyl)phenyl]-1-phenylindole

R=CH$_3$; Y=5-SO$_2$CH$_3$; Y$_1$=Y$_2$=Y$_3$=H;    Formula (I)

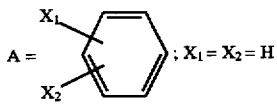

Purified by chromatography on silica gel (eluent: toluene 95%/ethyl acetate 5%).

Empirical formula: C$_{22}$H$_{19}$NO$_4$S$_2$; Melting point: 238° C.

EXAMPLE 21

1-(2-Thienyl)-2-[4-(methylsulfonyl)phenyl]indole

R=CH$_3$; Y$_1$=Y$_2$=Y$_3$=H;    Formula (I)

A = 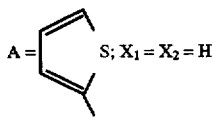 S; X₁ = X₂ = H

Purified by chromatography on silica gel (eluent: toluene 80%/ethyl acetate 20%) and by recrystallization from 5 volumes of acetonitrile.
Empirical formula: $C_{19}H_{15}NO_2S_2$; Melting point: 168° C.

EXAMPLE 22

1-[4-(N,N-Dimethylaminomethyl)phenyl]-2-[4-(methylsulfonyl)-phenyl]indole

R=CH₃; Y₁=Y₂=Y₃=H;   Formula (I)

A = 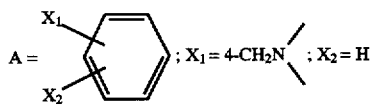 ; X₁ = 4-CH₂N(/\); X₂ = H

Purified by silica gel chromatography in two elutions (eluent: CH₂Cl₂ 95%/acetone 5%, then CHCl₃ 95%/isopropylamine 5%) and recrystallized from acetonitrile.
Empirical formula: $C_{24}H_{24}N_2O_2S$; Melting point: 147° C.

EXAMPLE 23

3-Methyl-2-[4-(methylsulfonyl)phenyl]-1-phenylindole

R=CH₃; Y₁=Y₂=H; Y₃=CH₃;   Formula (I)

A = 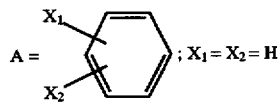 ; X₁ = X₂ = H

Empirical formula: $C_{22}H_{19}NSO_2$; Melting point: 224° C.

EXAMPLE 24

1-[4-(N,N-Dimethylaminomethyl)phenyl]-3-methyl-2-[4-(methylsulfonyl)phenyl]indole R=CH₃; Y₁=Y₂=H; Y₃=CH₃;   Formula (I)

A = 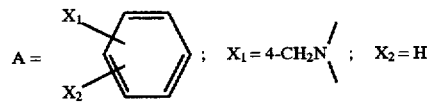 ; X₁ = 4-CH₂N(/\); X₂ = H

Purified by silica gel chromatography in two successive elutions (eluent: CH₂Cl₂ 80%/acetone 20% and CH₂Cl₂ 95%/methanol 5%).
Empirical formula: $C_{25}H_{26}N_2O_2S$; Melting point: 196° C.

EXAMPLE 25

5-Methyl-2-[4-(methylsulfonyl)phenyl]-1-phenylindole

R=CH₃; Y₁=5-CH₃; Y₂=Y₃=H;   Formula (I)

A = 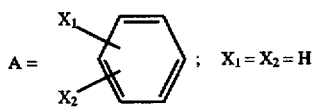 ; X₁ = X₂ = H

Empirical formula: $C_{22}H_{19}NO_2S$; Melting point: 152° C.

EXAMPLE 26

2-[4-(Methylsulfonyl)phenyl]-1-(3-pyridyl)indole

R=CH₃; Y₁=Y₂=Y₃=H;   Formula (I)

A = 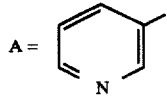

Empirical formula: $C_{20}H_{16}N_2O_2S$; Melting point: 171° C.

EXAMPLE 27

4,6-Dichloro-1-[4-(N,N-dimethylaminomethyl)phenyl]-2-[4-(methylsulfonyl)phenyl]indole R=CH₃; Y₁=4-Cl; Y₂=6-Cl; Y₃=H;   Formula (I)

A = 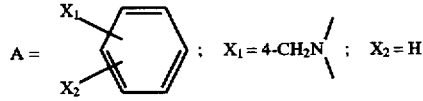 ; X₁ = 4-CH₂N(/\) ; X₂ = H

Empirical formula: $C_{24}H_{22}Cl_2N_2O_2S$; Melting point: 138° C.

EXAMPLE 28

4-(1-Phenyl-2-indolyl)benzenesulfonamide

R=NH₂; Y₁=Y₂=Y₃=H;   Formula (I)

A = 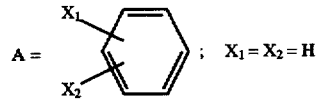 ; X₁ = X₂ = H

A solution of 16.6 g (0.048 mol) of 2-[4-(methylsulfonyl)phenyl]-1-phenylindole, prepared in Example 18, in 200 ml of anhydrous THF is cooled to 0° C. 20 ml (0.06 mol) of a 3M solution of methylmagnesium chloride in THF are added dropwise.

The temperature is allowed to return to room temperature. After a reaction time of 30 min, the mixture is cooled to 0° C. again and 72 ml (0.072 mol) of a 1M solution of tributylborane in THF are introduced dropwise. The temperature is allowed to return to room temperature. After a reaction time of 30 min, the mixture is refluxed for 18 h. The reaction medium is cooled to 0° C. again and a solution of 27.5 g of sodium acetate and 18.9 g of hydroxylamine-O-sulfonic acid in 120 ml of water is introduced.

The reaction is allowed to proceed for 3 h at room temperature. After decanting, the organic phase is diluted with ethyl acetate, washed with saturated NaHCO₃ solution and then with saturated NaCl solution, dried over MgSO₄ and concentrated. The compound obtained is purified by chromatography on silica gel (eluent: CHCl₃ 95%/isopropylamine 5%) and recrystallized from toluene to give 3.6 g of 4-(1-phenyl-2-indolyl)benzenesulfonamide.

Empirical formula: $C_{20}H_{16}N_2O_2S$; Melting point: 172° C.

The compound of Example 29 was prepared by following the procedure of Example 4.

EXAMPLE 29

4-(Methylsulfonyl)acetophenone 2,4-Difluorophenylhydrazone

R'=CH$_3$; Y$_1$=2-F; Y$_2$=4-F; Y$_3$=H    Formula (IV)

Empirical formula: $C_{15}H_{14}F_2N_2O_2S$; Melting point: 170° C.

The compound of Example 30 was prepared by following the procedure of Example 10.

EXAMPLE 30

5,7-Difluoro-2-[4-(methylsulfonyl)phenyl]indole

R'=CH$_3$; Y$_1$=5-F; Y$_2$=7-F; Y$_3$=H    Formula (II)

Empirical formula: $C_{15}H_{11}F_2NO_2S$; Melting point: 252°–254° C.

PHARMACOLOGY

Inhibition of the COX-1 and COX-2 Enzymatic Activities

The molecule studied is preincubated for 10 minutes at 25° C. with 2 U of COX-1 (purified enzyme from ram seminal vesicles) or 1 U of COX-2 (purified enzyme from ewe placenta). Arachidonic acid (6 µM for COX-1, 4 µM for COX-2) is added to the reaction medium and incubation is carried out for 5 minutes at 25° C. When incubation has ended, the enzymatic reaction is stopped by the addition of 1N HCl and the PGE2 produced is determined by EIA.

The results are expressed as the percentage inhibition of the COX-1 and COX-2 enzymatic activities and correspond to mean (±) standard deviations from the average of 4 determinations.

| Example | % inhibition of the COX-2 activity | | % inhibition of the COX-1 activity | |
| --- | --- | --- | --- | --- |
|  | 10$^{-5}$ M | 10$^{-7}$ M | 10$^{-5}$ M | 10$^{-7}$ M |
| 16 | 83 ± 2 | 29 ± 2 | 36 ± 14 | 4 ± 4 |
| 17 | 89 ± 2 |  | 29 ± 5 | 2 ± 2 |
| 18 | 88 ± 2 |  | 23 ± 6 | 2 ± 2 |
| 19 | 95 ± 0 |  |  |  |

TOXICOLOGY

The first toxicology studies performed show that the products of the Examples do not induce a deleterious effect in the rat after the oral absorption of doses ranging up to 300 mg/kg.

What is claimed is:

1. A 1,2-diarylindole compound of formula (I):

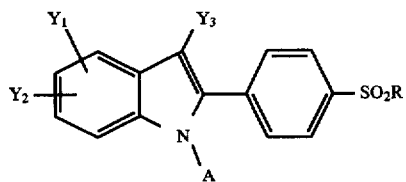

Formula (I)

in which:

R is:
 a lower alkyl group having 1 to 6 carbon atoms,
 a lower haloalkyl group having 1 to 6 carbon atoms, or
 a group —NH$_2$;

A is:
 an aromatic ring:

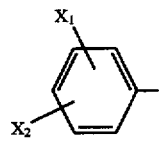

in which X$_1$ and X$_2$ independently are:
 the hydrogen atom,
 a halogen atom,
 a lower alkyl group having 1 to 6 carbon atoms,
 a trifluoromethyl group,
 a group (CH$_2$)$_n$NR$_1$R$_2$ in which:
  n is an integer from 0 to 2 and
  R$_1$ and R$_2$ independently are the hydrogen atom or a lower alkyl group having 1 to 6 carbon atoms,
 a lower O-alkyl group having 1 to 6 carbon atoms, or
 a group SO$_2$R, R being as defined above,
or else X$_1$ and X$_2$ together form a methylenedioxy group;
A is also a thiophene or pyridine heterocycle;
Y$_1$ and Y$_2$ independently are:
 the hydrogen atom,
 a halogen atom,
 a lower alkyl group having 1 to 6 carbon atoms, or
 a group SO$_2$R, R being as defined above; and
Y$_3$ is:
 the hydrogen atom or
 a lower alkyl group having 1 to 6 carbon atoms.

2. A compound of formula (I) according to claim 1 in which:
R is a lower alkyl group having 1 to 6 carbon atoms;
A is an aromatic ring:

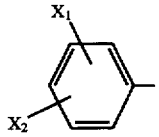

in which X$_1$ and X$_2$ independently are:
 the hydrogen atom,
 a halogen atom,
 a lower alkyl group having 1 to 6 carbon atoms, or
 a group (CH$_2$)$_n$NR$_1$R$_2$ in which:
  n is equal to 1 and $R_1$ and $R_2$ are a lower alkyl group having 1 to 6 carbon atoms;

A is also a thiophene heterocycle;

$Y_1$ and $Y_2$ independently are:
the hydrogen atom,
a halogen atom,
a lower alkyl group having 1 to 6 carbon atoms, or
a group $SO_2R$, R being as defined above; and $Y_3$ is:
the hydrogen atom or
a lower alkyl group having 1 to 6 carbon atoms.

3. A compound according to claim 1 wherein R is the methyl group.

4. A compound according to claim 1 wherein $X_1$ is selected from the group consisting of the hydrogen atom, a halogen atom and the methyl group and $X_2$ is the hydrogen atom.

5. A compound according to claim 1 wherein $Y_1$ and $Y_2$ are the hydrogen atom.

6. A compound according to claim 1 which is selected from the group consisting of:

1-(4-fluorophenyl)-2-[4-(methylsulfonyl)phenyl]indole

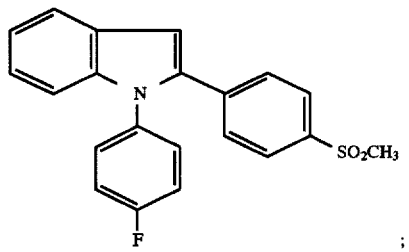

;

1-(4-chlorophenyl)-2-[4-(methylsulfonyl)phenyl]indole

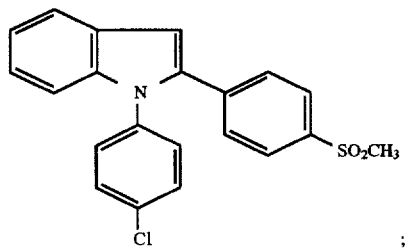

;

1-(4-methylphenyl)-2-[4-(methylsulfonyl)phenyl]indole

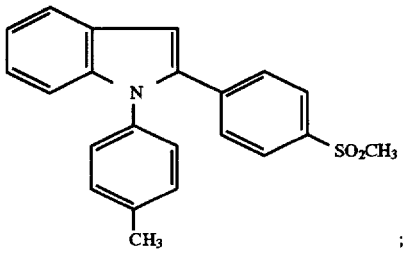

; and 1-phenyl-2-[4-(methylsulfonyl)phenyl]indole

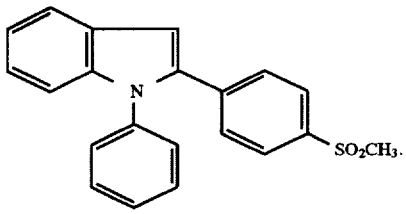

.

7. A pharmaceutical composition which comprises a pharmaceutically effective amount of a compound of formula (I) as defined in claim 1 incorporated in a pharmaceutically acceptable excipient, vehicle or carrier.

8. A pharmaceutical composition with anti-inflammatory and analgesic activity which comprises a pharmaceutically effective amount of a compound of formula (I) as defined in of claim 1 incorporated in a pharmaceutically acceptable excipient, vehicle or carrier.

9. A pharmaceutical composition according to claim 7 which is presented in the form of gelatin capsules or tablets containing a dose of 1 mg to 1000 mg.

10. A pharmaceutical composition according to claim 7 which is presented in the form of injectable preparations containing a dose of 0.1 mg to 500 mg.

11. A method for treating inflammation in a mammal which comprises administering an anti-inflammatory effective amount of a compound of formula I as defined in claim 1 to said mammal.

12. A method, for treating pain in a mammal which comprises administering an effective amount of a compound of formula I as defined in claim 1 to said mammal.

* * * * *